US008969598B2

(12) United States Patent
Terrill et al.

(10) Patent No.: US 8,969,598 B2
(45) Date of Patent: *Mar. 3, 2015

(54) PRODUCTION OF CYCLIC ACETALS OR KETALS USING LIQUID-PHASE ACID CATALYSTS

(75) Inventors: Daniel Latham Terrill, Bristol, TN (US); Brian David McMurray, Hiltons, VA (US); Damon Ray Billodeaux, Longview, TX (US); James Lon Little, Kingsport, TN (US); Adam Scott Howard, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 92 days.

This patent is subject to a terminal disclaimer.

(21) Appl. No.: 13/168,374

(22) Filed: Jun. 24, 2011

(65) Prior Publication Data
US 2012/0330033 A1 Dec. 27, 2012

(51) Int. Cl.
C07D 317/12 (2006.01)
(52) U.S. Cl.
CPC .................................. *C07D 317/12* (2013.01)
USPC ............ 549/430; 549/374; 549/369; 549/453
(58) Field of Classification Search
USPC .................. 549/352, 374, 347, 453, 430, 369
See application file for complete search history.

(56) References Cited

U.S. PATENT DOCUMENTS

| 2,425,042 A | 8/1947 | McNamee et al. |
| 2,429,878 A | 10/1947 | Gresham et al. |
| 2,486,024 A | 10/1949 | Hearne et al. |
| 3,275,680 A | 9/1966 | Holzrichter et al. |
| 4,024,159 A | 5/1977 | Peterson |

(Continued)

FOREIGN PATENT DOCUMENTS

| CA | 1 254 190 | 5/1989 |
| DE | 419223 C | 9/1925 |

(Continued)

OTHER PUBLICATIONS

William L. Luyben and Cheng-Ching Yu (Reactive Distillation Design and Control, 2008, John Wiley & Sons, p. 514-517).*

(Continued)

*Primary Examiner* — Kristin Vajda
*Assistant Examiner* — Valerie Rodriguez-Garcia
(74) *Attorney, Agent, or Firm* — Dennis V. Carmen

(57) ABSTRACT

A process for making a cyclic compounds such as cyclic acetal or cyclic ketones by feeding aldehyde or ketone compounds and polyhydroxyl compounds to a reaction vessel at a molar ratio of polyhydroxyl compounds to aldehyde or ketone compounds of at least 3:1, reacting these compounds in the presence of a homogeneous acid catalyst to generate a liquid phase homogeneous reaction mixture containing the acid catalyst without separating water from the reaction mixture as it is being formed in the reaction mixture, withdrawing the liquid phase homogeneous reaction mixture from the reaction vessel as a liquid product stream, and feeding the liquid reaction product stream to a distillation column to separate cyclic acetal compounds from unreacted polyhydroxyl compounds, and optionally recycling back the unreacted polyhydroxyl compounds and/or acid catalyst to the reaction vessel. The process produces cyclic acetal compounds in high yields. The process is also suitable to make cyclic ketals from ketone compounds.

22 Claims, 1 Drawing Sheet

(56) References Cited

U.S. PATENT DOCUMENTS

| | | |
|---|---|---|
| 4,038,175 A | 7/1977 | Bhasin |
| 4,062,898 A | 12/1977 | Dubeck et al. |
| 4,071,568 A | 1/1978 | Onoda et al. |
| 4,088,700 A | 5/1978 | Watts |
| 4,169,959 A | 10/1979 | Arpe |
| 4,308,403 A | 12/1981 | Knifton |
| 4,317,943 A | 3/1982 | Knifton |
| 4,356,327 A | 10/1982 | Knifton |
| 4,357,477 A | 11/1982 | Knifton |
| 4,375,394 A | 3/1983 | Devon |
| 4,390,734 A | 6/1983 | Knifton |
| 4,430,253 A | 2/1984 | Dubeck |
| 4,435,595 A | 3/1984 | Agreda et al. |
| 4,478,017 A | 10/1984 | Brown et al. |
| 4,479,017 A | 10/1984 | Ayusawa et al. |
| 4,482,753 A | 11/1984 | Tai-Huang et al. |
| 4,484,009 A | 11/1984 | Ghenassia et al. |
| 4,537,980 A | 8/1985 | Greenshields |
| 4,568,780 A | 2/1986 | Knifton |
| 4,617,287 A | 10/1986 | Lyons |
| 4,618,729 A | 10/1986 | Duggan et al. |
| 4,663,489 A | 5/1987 | Duggan et al. |
| 4,692,426 A | 9/1987 | Duggan et al. |
| 4,847,425 A | 7/1989 | Degner et al. |
| 4,895,818 A | 1/1990 | Duggan et al. |
| 4,895,987 A | 1/1990 | Duggan et al. |
| 4,939,294 A | 7/1990 | Agreda et al. |
| 5,319,148 A | 6/1994 | Karcher et al. |
| 5,362,918 A | 11/1994 | Aizawa et al. |
| 5,399,631 A | 3/1995 | Egawa et al. |
| 5,446,208 A | 8/1995 | Koshino et al. |
| 5,446,210 A | 8/1995 | Hees et al. |
| 5,523,491 A | 6/1996 | Egawa et al. |
| 5,589,597 A | 12/1996 | Egawa et al. |
| 5,616,736 A | 4/1997 | Thigpen |
| 5,720,895 A | 2/1998 | Nakagawa et al. |
| 5,763,691 A | 6/1998 | Kawabe |
| 5,780,687 A | 7/1998 | Holderich et al. |
| 5,821,391 A | 10/1998 | Holderich et al. |
| 5,866,735 A | 2/1999 | Cheung |
| 5,886,198 A | 3/1999 | Ogawa et al. |
| 5,917,059 A | 6/1999 | Bruchmann et al. |
| 5,935,896 A | 8/1999 | Dupuis et al. |
| 6,013,844 A | 1/2000 | Heineke et al. |
| 6,015,875 A | 1/2000 | Smith et al. |
| 6,028,215 A | 2/2000 | Bessling et al. |
| 6,080,897 A | 6/2000 | Kawabe |
| 6,087,539 A | 7/2000 | Yamasaki et al. |
| 6,124,479 A | 9/2000 | Hinoue et al. |
| 6,136,576 A | 10/2000 | Diaz-Torres |
| 6,143,908 A | 11/2000 | Hinoue et al. |
| 6,166,240 A | 12/2000 | Jiang et al. |
| 6,207,850 B1 | 3/2001 | Jiang et al. |
| 6,232,512 B1 | 5/2001 | Haas et al. |
| 6,265,623 B1 | 7/2001 | Morawietz et al. |
| 6,291,725 B1 | 9/2001 | Chopade |
| 6,380,419 B2 | 4/2002 | Kawabe |
| 6,458,992 B1 | 10/2002 | Lederer et al. |
| 6,518,464 B2 | 2/2003 | Therre et al. |
| 6,548,681 B1 * | 4/2003 | Chopade et al. ............ 549/372 |
| 6,657,089 B1 | 12/2003 | Nagasawa et al. |
| 6,670,489 B2 | 12/2003 | Koyama et al. |
| 6,713,640 B2 | 3/2004 | Miller et al. |
| 6,969,779 B2 | 11/2005 | Brewer et al. |
| 7,030,277 B2 | 4/2006 | Groten et al. |
| 7,060,372 B2 | 6/2006 | Fryd et al. |
| 7,071,362 B2 | 7/2006 | Sugawara et al. |
| 7,160,524 B2 | 1/2007 | Lederer et al. |
| 7,301,055 B2 | 11/2007 | Hoffmockel et al. |
| 7,321,052 B2 | 1/2008 | Miller et al. |
| 7,488,851 B2 | 2/2009 | Egidio Rodrigues et al. |
| 7,498,451 B2 | 3/2009 | Haderlein et al. |
| 7,534,922 B2 * | 5/2009 | Goring et al. ............ 568/594 |
| 7,754,900 B2 | 7/2010 | Siegert et al. |
| 2006/0129000 A1 | 6/2006 | Goring et al. |
| 2006/0199970 A1 | 9/2006 | Miller et al. |
| 2008/0283384 A1 | 11/2008 | Lang et al. |
| 2010/0048940 A1 | 2/2010 | Tulchinsky et al. |
| 2010/0099894 A1 | 4/2010 | Dubois et al. |
| 2010/0158780 A1 | 6/2010 | Galligan et al. |
| 2010/0228065 A1 | 9/2010 | Cheung et al. |
| 2010/0261936 A1 | 10/2010 | Okumura et al. |
| 2010/0292491 A1 | 11/2010 | Selifonov et al. |
| 2011/0034739 A1 | 2/2011 | Stochniol et al. |
| 2011/0207969 A1 | 8/2011 | Olken et al. |
| 2012/0330032 A1 * | 12/2012 | Terrill et al. .................. 549/352 |

FOREIGN PATENT DOCUMENTS

| | | |
|---|---|---|
| DE | 3328561 A1 | 2/1985 |
| DE | 238 232 A1 | 8/1986 |
| DE | 19648960 A1 | 5/1998 |
| DE | 10036423 A1 | 3/2001 |
| EP | 0 168 989 A1 | 1/1986 |
| EP | 0 169 666 B1 | 1/1986 |
| EP | 0 271 091 A1 | 6/1988 |
| EP | 0 312 659 A1 | 4/1989 |
| EP | 0499055 A2 | 8/1992 |
| EP | 0616994 A2 | 9/1994 |
| EP | 0 624 563 A1 | 11/1994 |
| EP | 0696564 A1 | 2/1996 |
| EP | 1 236 511 A1 | 9/2002 |
| FR | 2 906 246 A1 | 3/2008 |
| GB | 1020500 A | 2/1966 |
| JP | 52073810 A | 6/1977 |
| JP | 56166186 A | 12/1981 |
| JP | 58198431 A | 11/1983 |
| JP | 5155878 A | 6/1993 |
| JP | 5271217 A | 10/1993 |
| JP | 6128184 A | 5/1994 |
| JP | 2001072636 A | 3/2001 |
| JP | 4287546 B2 | 7/2009 |
| WO | WO 01/19763 A1 | 3/2001 |
| WO | WO 03/002547 A1 | 1/2003 |
| WO | WO 2010/027663 | 3/2010 |

OTHER PUBLICATIONS

Dhale et al. (Chemical Engineering Science, 2004, 59, p. 2881-2890).*
Hao et al. (J. chem. Technol. Biotechnol. 2006, 81, pp. 102-108).*
Stichlmair and Frey (Chem. Eng. Technol. 22 (1999) 2; p. 95-103).*
Knifton "Syngas reactions: Part VIII: The preparation of glycol monoalkyl ethers," Journal of Molecular Catalysis 1985, 30, pp. 281-297.
Jakab et al. "Synthesis, regioselective hydrogenolysis, partial hydrogenation, and conformational study of dioxane and dkoxane-type (9-anthracenyl)methylene acetals of sugars," Carbohydrate Research 2009, 344, pp. 2444-2453.
Broekhuis et al. "Recovery of Propylene Glycol from Dilute Aqueous Solutions via Reversible Reaction with Aldehydes" Ind. Eng. Chem. Res. 1994, 33, pp. 3230-3237.
Dhale et al. "Propylene Glycol and Ethylene Glycol Recovery from Aqueous Solution via Reactive Distillation" Chemical Engineering Science, 2004, 59, pp. 2881-2890.
Hao et al. "Downstream processing of 1,3-propanediol fermentation broth" J. Chem. Technol. Biotechnol. 2006, 81, pp. 102-108.
Howard et al. "Hydrogenolysis of Ketals" J. Org. Chem., 1961 26(4), pp. 1026-1028.
Osman et al. "Cyclic Acetal Formation Between 2-Pyridinecarboxaldehyde and y-Hydroxy-a,b-Acetylenic Esters" Tetrahedron Lett. 2008, 49 (46) pp. 6550-6552.
Zajac et al. "Reaction of 2-Butynal Diethyl Acetal with Lithium Aluminum Hydride" J. Org. Chem., 1975 40(4), pp. 530-531.
Astle et al. "Catalysis with Cation-Exchange Resins, Preparation of 1,3 Dioxolanes and 1,3,6-Trioxocanes", Industrial and Engineering Chemistry, Apr. 1954, pp. 787-791.
Singh et al. "Production of Butyl Acetate by Catalytic Distillation. Theoretical and Experimental Studies" Ind. Eng. Chem. Res. 2005, 44, pp. 3042-3052.

(56) References Cited

OTHER PUBLICATIONS

Venimadhavan et al. "A Novel Distillate Policy for Batch Reactive Distillation with Application to the Production of Butyl Acetate" Ind. Eng. Chem. Res. 1999, 38, pp. 714-722.
Chadda et al. "Feasibility and Synthesis of Hybrid Reactive Distillation Systems" AIChE Journal, Dec. 2002, vol. 48, No. 12, pp. 2754-2768.
Hibbert et al., J. Am. Chem. Soc. 1924, 46(5), pp. 1283-1290.
Sulzbacher et al., J. Am. Chem. Soc. 1948, 70(8), pp. 2827-2828.
Bronsted and Grove, J. Am. Chem. Soc. 1930, 52(4), pp. 1394-1403.
Van Duzee et al., J. Am. Chem. Soc. 1935, 57, p. 147.
Bonner et al., J. Am. Chem. Soc., Perkins Trans. 1981, pp. 1807-1810.
Tkachenko et al. "Research in the Field of Furan Acetal Compounds. XII. Features of the Vapor-Phase Hydrogenation of Disubstituted 1,3-Dioxolanes", Chemistry and Technology of Furan Compounds, 1985, pp. 59-64.
Public Dow literature, "Dow Technology Licensing—METEOR™ Ethylene Oxide/Glycol Process Technology," http://www.dow.com/licensing/offer/meteor.htm (downloaded and printed from the internet on Aug. 24, 2011).
Public Shell literature, "Factsheets: OMEGA and ethylene oxide/ethylene glycol technology," http://www.shell.com/home/content/chemicals/aboutshell/media_centre/factsheets/omega/ (downloaded and printed from the internet on Aug. 24, 2011).
Public website at http://globalbiochemna.com/, Global BioChem Technology Group (GBT), Product Information, "About Us, and Glycols Project/Polyol Chemicals" (downloaded and printed from the internet on Aug. 24, 2011).
Public Dow literature, Dow Product Safety Assessment, "Ethylene Glycol Butyl Ether" (EGBE), at http://www.dow.com/productsafety, Product Safety Assessment Finder. (downloaded and printed from the internet on Aug. 24, 2011).
Kul'nevich et al., Khimiya Geterotsiklicheskikh Soyedinenii, No. 8, 1977, pp. 1026-1029.
U.S. Appl. No. 13/168,229, filed Jun. 24, 2011.
U.S. Appl. No. 13/168,274, filed Jun. 24, 2011.
U.S. Appl. No. 13/168,304, filed Jun. 24, 2011.
U.S. Appl. No. 13/168,330, filed Jun. 24, 2011.
U.S. Appl. No. 13/168,349, filed Jun. 24, 2011.
U.S. Appl. No. 13/168,361, filed Jun. 24, 2011.
Coelho, Antonio Carlos Vieira, et al.; "Surface Area, Crystal Morphology and Characterization of Transition Alumina Powders from a New Gibbsite Precursor"; Materials Research, vol. 10, No. 2, pp. 183-189, (2007), XP002683656.
Hudson, L. Keith, et al.; "Aluminum Oxide", Internet Citation XP-002596245, pp. 1-40, Jun. 15, 2000, URL: http://onlinelibrary.wiley.com/doi/10.
Hibbert, H., et al.: Studies on the reactions relating to carbohydrates and polysaccharides. X. Synthesis and relative stability of cyclic acetals from 1, 2- and 1, 3-glycols; Journal of the American Chemistry Society, vol. 46, No. 5, 1924. pp. 1283-1290, XP002621973, pp. 1286, 1287, "Experimental Part".
Notification of Transmittal of the International Search Report and the Written Opinion of the International Searching Authority dated Jun. 19, 2012 for International Application No. PCT/US2012/043085.
Notification of Transmittal of the International Search Report and the Written Opinion of the International Searching Authority dated Jun. 14, 2012 for International Application No. PCT/US2012/042378.
Notification of Transmittal of the International Search Report and the Written Opinion of the International Searching Authority dated Jun. 8, 2012 for International Application No. PCT/US2012/041459.
Notification of Transmittal of the International Search Report and the Written Opinion of the International Searching Authority dated Sep. 3, 2012 for International Application No. PCT/US2012/042458.
Notification of Transmittal of the International Search Report and the Written Opinion of the International Searching Authority dated Sep. 11, 2012 for International Application No. PCT/US2012/043071.
Notification of Transmittal of the International Search Report and the Written Opinion of the International Searching Authority dated Oct. 15, 2012 for International Application No. PCT/US2012/042453.
Notification of Transmittal of the International Search Report and the Written Opinion of the International Searching Authority dated Sep. 14, 2012 for International Application No. PCT/US2012/043093.
USPTO Office Action dated Nov. 26, 2012 for co-pending U.S. Appl. No. 13/168,229.
Luyben, William L., et al.; "Reactive Distillation Design and Control", John Wiley & Sons, 2008, p. 514-517.
Stichlmair, Johann, et al.; "Reactive Distillation Processes"; Chemical Engineering Technology, 22 (1999) 2; pp. 95-103.
Copending U.S. Appl. No. 14/337,544, filed Jul. 22, 2014; Daniel Latham Terrill et al.
USPTO Notice of Allowance dated Aug. 4, 2014 for co-pending U.S. Appl. No. 13/168,229.
Copending U.S. Appl. No. 14/459,875, filed Aug. 14, 2014; Damon Ray Billodeaux et al.
USPTO Office Action dated Jul. 1, 2013 for co-pending U.S. Appl. No. 13/168,229.
USPTO Office Action dated Aug. 15, 2013 for co-pending U.S. Appl. No. 13/168,330.
USPTO Office Action dated Nov. 1, 2013 for co-pending U.S. Appl. No. 13/168,274.
USPTO Office Action dated Nov. 1, 2013 for co-pending U.S. Appl. No. 13/168,304.
USPTO Office Action dated Nov. 1, 2013 for co-pending U.S. Appl. No. 13/168,349.
USPTO Office Action dated Nov. 4, 2013 for co-pending U.S. Appl. No. 13/168,361.
USPTO Office Action dated Feb. 26, 2014 for co-pending U.S. Appl. No. 13/168,229.
USPTO Office Action dated Jun. 4, 2014 for co-pending U.S. Appl. No. 13/168,304.
USPTO Office Action dated Jun. 5, 2014 for co-pending U.S. Appl. No. 13/168,349.
USPTO Notice of Allowance dated Jun. 17, 2014 for co-pending U.S. Appl. No. 13/168,361.
Copending U.S. Appl. No. 14/307,956, filed Jun. 18, 2014; Damon Ray Billodeaux et al.
USPTO Office Action dated Jul. 2, 2014 for co-pending U.S. Appl. No. 13/168,274.
USPTO Notice of Allowance dated Jul. 9, 2014 for co-pending U.S. Appl. No. 13/168,330.

\* cited by examiner

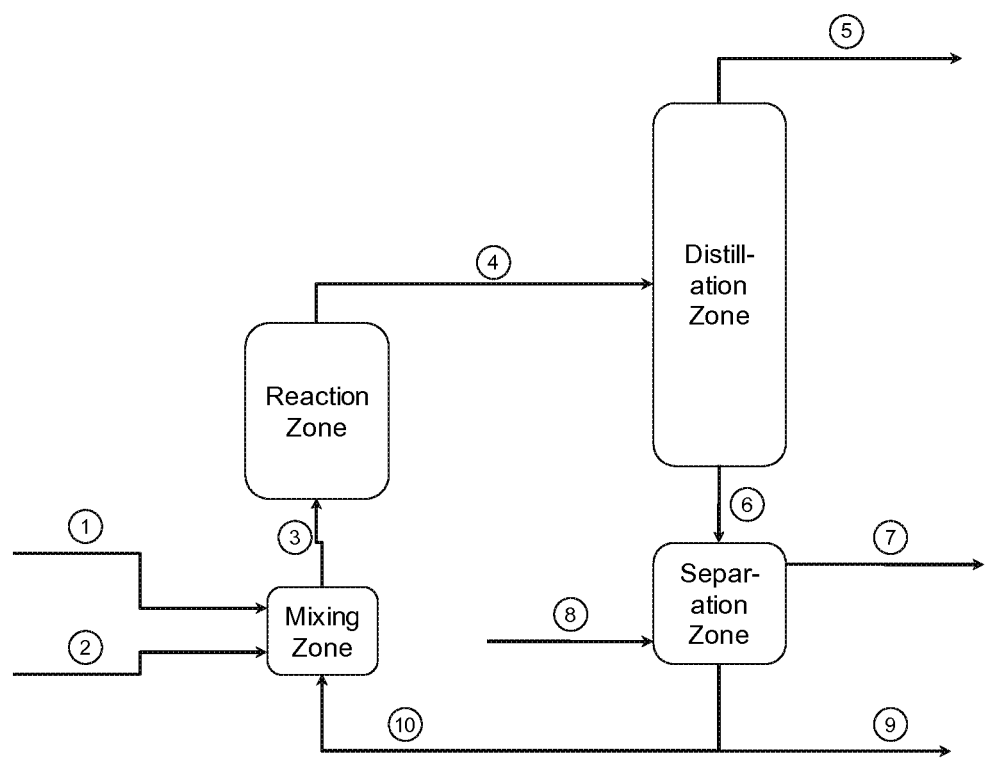

PRODUCTION OF CYCLIC ACETALS OR KETALS USING LIQUID-PHASE ACID CATALYSTS

1. FIELD OF THE INVENTION

The invention relates to the production of cyclic acetals or ketals at high yields.

2. BACKGROUND OF THE INVENTION

Ether alcohols, such as 2-butoxyethanol, have important industrial functions in such products such as cleaning supplies and coating materials. In the past, the manufacture of these products has been based on a process relying on a reaction between an alcohol and ethylene oxide. This conventional process has proven to be somewhat inefficient, in that it produces various undesirable byproducts along with the ether alcohols.

Monoether glycols can also be manufactured in a reaction between aliphatic aldehydes and ethylene glycol, instead of ethylene oxide, under acidic conditions in order to produce cyclic acetals. The acetal of ethylene glycol and butyraldehyde, for example, is described by Hibbert and Timm (Hibbert, H.; Timm, J. A. *J. Am. Chem. Soc.* 1924, 46(5), 1283-1290) and is achieved with a maximum yield of 50%. These cyclic acetals, or ketals when a ketone is substituted for the aldehyde, can then be subjected to hydrogenolysis in the presence of palladium and phosphoric acid catalysts. Such a process is described in U.S. Pat. No. 4,484,009.

The reaction of the polyhydroxyl compounds with aldehydes or ketones is an equilibrium reaction with the acetal product and by-product water. Yield of acetal or ketal is reduced via hydrolysis of the acetal by the co-product water. Thus, it is desirable to remove water from the reaction system to increase yield of the acetal.

The separation of water from the reaction mixture has been difficult since it often forms an azeotrope with the aldehyde reactants and with the cyclic acetal products. Entrainers have been employed to remove water through azeotropic distillation. Sulzbacher and coworkers, for example, describe removing the water by using benzene during the preparation of a number of acetals of ethylene glycol (Sulzbacher, M. et.al. *J. Am. Chem. Soc.* 1948, 70(8), 2827-2828). The environmental and health impact of benzene is an obvious concern in this method. Dessicants such as calcium chloride (DE 419223; Brönsted and Grove *J. Am. Chem. Soc.* 1930, 52(4), 1394-1403) may be employed in the reaction vessel to remove water as it is formed, but disposal of the generated solid waste is an economic and environmental concern.

Another method as described by Astle and coworkers, involves heating the glycol and aldehyde over an heterogeneous acidic resin and distilling out the acetal and water as they are formed (Astle, M. J. et al, *Ind. Eng. Chem.* 1954, 46(4), 787-791). This method generally had low yields with one example for the manufacture of 2-butoxyethanol reported as having a yield of about 92% using a molar ratio of ethylene glycol to butyraldehyde of about 1.3:1. In these reactions, water was being separated from the reaction mixture in the flask as the water was being formed, and upon completion, the reaction mixture in the flask was filtered and phase separated. The removal of water from the reaction mixture as it was being formed follows from the understanding that the reaction of the polyhydroxyl compounds with aldehydes is an equilibrium reaction with the acetal product and by-product water, and the yield of acetal is reduced via hydrolysis of the acetal by the co-product water or can be increased with the removal of water as it is formed.

One pot reaction systems have also been reported, that is, reacting an aldehyde and a polyhydroxyl with hydrogen in the presence of a noble metal catalyst directly to the desired ether alcohol. For example, U.S. Pat. No. 5,446,210 describes a process for the production of hydroxy ether hydrocarbons in a one pot system by reacting a polyhydroxyl with an aldehyde and hydrogen in the presence of a noble metal catalyst where the molar ratio of polyhydroxyl to aldehyde compound ranges from 5:1 to 1:5 is described, but with these molar ratios, the yield was low in the range of 35 to 50% when including the bis- types of by-products with low selectivity to the mono-ether products.

US Publication No. 2010/0048940 also describes a one pot system in which a polyhydroxyl and a aldehyde compound and hydrogen are reacted together in the presence of a hydrogenolysis catalyst to provide the polyhydroxyl ether, where the molar ratio of polyhydroxyl to aldehyde exceeds 5:1 to improve selectivity and yield. An example of a two stage process in which the acetal compound was first synthesized and then subjected to hydrogenolysis was reported without describing the yield value of the acetal produced, although the yield to the 2-butoxyethanol by hydrogenolysis of the acetal was reported as having a selectivity of about 61%.

In U.S. Pat. No. 5,917,059 to BASF Aktiengesellschaft, the authors generate cyclic acetals and ketals by reacting a molar excess of aldehydes and ketones with polyhydroxyl compounds in the presence of an acid catalyst. The water is removed by continuously distilling unreacted aldehydes or ketone starting materials, thus co-distilling the formed water in the water/aldehyde azeotrope, and further replacing the distilled aldehyde or ketone with fresh aldehyde or ketone. The aldehydes and ketones act not only as a reactant but also as a medium for transporting the water produced in the reaction. This method requires large excess of aldehyde (e.g. 4:1 molar ratio of aldehyde:alcohol) to be successful.

Reactive distillation is employed in U.S. Pat. Nos. 6,015, 875 and 7,534,922 B2 to generate low boiling acetals. The authors make use of heterogeneous acids in the packing of the column and feed low boiling starting materials such as methanol, ethanol, formaldehyde, and acetaldehyde. The formed acetals are removed overhead above the distillation reaction zone and the co-product water is removed below the distillation reaction zone. This method limits the types of usable reactants to those producing materials that boil at a temperature lower than water.

As can be seen from the available literature, there exists a continued need to produce cyclic acetal or ketal compounds in high yield using a simple economic process.

3. BRIEF SUMMARY OF THE INVENTION

Cyclic acetals and ketals can now be produced in high yield in a simple method which does not require removal of water as it is generated. Contrary to the expectation that yields would be unacceptably low unless water is removed during its formation as a by-product, the process of the invention allows one to react all starting materials in the liquid phase in one reaction vessel to make a reaction mixture which is removed in the liquid phase and subsequently distilled to produce the desired cyclic acetal or ketal in high yields.

There is now provided a continuous process for making a cyclic acetal or ketal compounds comprising:

a. feeding a carbonyl composition comprising an aldehyde compound, a ketone compound, or a combination thereof, and a polyhydroxyl composition comprising a polyhydroxyl compound, to a reaction vessel at a molar ratio of all polyhydroxyl compounds to all carbonyl compounds fed to the reaction vessel of at least 3:1; and b. in a reaction vessel, reacting the carbonyl composition with the polyhydroxyl compound in the presence of a homogeneous acid catalyst to generate a liquid phase homogeneous reaction mixture in the reaction vessel comprising cyclic compounds, water, acid catalyst, and unreacted polyhydroxyl compound; and c. without separating water from the reaction mixture as it is being formed in the reaction mixture, continuously withdrawing the liquid phase homogeneous reaction mixture from the reaction vessel as a liquid product stream; and d. feeding the liquid reaction product stream directly or indirectly to a distillation column to separate cyclic compounds from unreacted polyhydroxyl compounds and withdrawing from the distillation column an overhead product stream and a bottoms stream, wherein the overhead product stream comprises cyclic compounds, unreacted carbonyl compounds and water and is rich in the concentration of cyclic compounds by moles relative to the bottoms stream, and the bottoms stream comprises unreacted polyhydroxyl compounds and acid catalyst and is rich in the concentration of unreacted polyhydroxyl compounds by moles relative to the overhead product stream;

wherein the selectivity to cyclic compounds in the overhead product stream is at least 80%.

The yield of cyclic acetal or ketal compounds taken in an overhead product stream can also be at least 80%.

In the process of the invention, one may also recycle to the reaction vessel at least a portion of unreacted polyhydroxyl compounds withdrawn from the distillation column in the bottoms stream. Reaction by-products other than water may also be withdrawn from the bottoms stream to produce a polyhydroxyl rich stream and an organic by-product rich stream, following which at least a portion of the polyhydroxyl compounds and acid catalyst in the polyhydroxyl rich stream can be recycled to the reaction vessel.

4. BRIEF DESCRIPTION OF THE DRAWINGS

FIG. 1 is a process flow diagram for the production of cyclic acetal or ketal compounds in a reaction vessel followed by distillation, separation, and recycling a portion of polyhydroxyl compounds to the reaction vessel.

5. DETAILED DESCRIPTION OF THE INVENTION

There is now provided a continuous process for making cyclic compounds. By a cyclic compound is meant a compound having a ring structure that has two oxygen atoms in the ring structure that are single bonded to the same carbon atom in the ring structure. The cyclic compounds can be cyclic acetal compounds or cyclic ketal compounds. The cyclic compounds are made by feeding carbonyl compounds and a polyhydroxyl composition comprising a polyhydroxyl compound, to a reaction vessel at a molar ratio of all polyhydroxyl compounds and all aldehyde or ketone compounds fed to the reaction vessel of at least 3:1. By carbonyl compounds is meant aldehyde compounds, ketone compounds (depending upon whether one desires to make an acetal or ketal), or a mixture of the two.

The carbonyl composition fed to the reaction vessel contains one or more types of aldehyde or ketone compounds. Aldehyde compounds contain at least one aldehyde functionality. The aldehyde and ketone compounds can be represented by the Formula I:

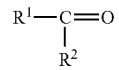

in which $R^1$ and $R^2$ are independently hydrogen or a $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, and wherein $R^1$ and $R^2$ are optionally connected through one or more carbon atoms, and wherein the alkyl, alkenyl, aryl, and cycloalkyl groups of $R^1$ and $R^2$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof; and wherein when one of $R^1$ or $R^2$ is hydrogen, the compound will be an aldehyde and wherein when neither $R^1$ and $R^2$ are hydrogen the compound is a ketone.

The aldehyde compound may have, if desired, at least one aldehyde functional group wherein the aldehyde carbon atom is bonded to a (i) branched or unbranched $C_1$-$C_9$ alkyl group or (ii) an aryl or alicyclic group which is optionally substituted with a branched or unbranched $C_1$-$C_9$ alkyl group.

Examples of an aldehyde compounds include, but are not limited to, benzaldehyde, acetaldehyde, propionaldehyde, butyraldehyde, isobutyraldehyde, pentaldehyde, 2-methylbutyraldehyde, 3-methylbutyraldehyde, n-pentanal, isopentanal, hexyldehyde, heptaldehyde, 2-ethylhexyldehyde, octanal, nonanal, n-decanal, 2-methylundecanal, lauryl aldehyde, myristyl aldehyde, cetyl aldehyde, stearyl aldehyde, behenyl aldehyde, glutaraldehyde, acrolein, crotonaldehyde, oleyl aldehyde, linoleyl aldehyde, linolenyl aldehyde, erucyl aldehyde, cinnamaldehyde, 1,3-cyclohexanedicarboxaldehyde, 1,4-cyclohexanedicarboxaldehyde, and combinations thereof.

Examples of ketone compounds include, but are not limited to, acetone, methyl ethyl ketone (2-butanone), methyl propyl ketone (2-pentanone), methyl isopropyl ketone (3-methyl-2-butanone), methyl isobutyl ketone (4-methyl-2-pentanone), 2-hexanone, 2-heptanone(methyl amyl ketone), 2-octanone, and acetophenone, and combinations thereof.

The polyhydroxyl composition fed to the reaction vessel contains one or more types of polyhydroxyl compounds. Polyhydroxyl compounds have at least two hydroxyl (—OH) functionalities. The polyhydroxyl compounds may contain ether or ester linkages in the longest carbon chain.

Suitable polyhydroxyl compounds for the present invention include, but are not limited to ethylene glycol, 1,2-propanediol, 1,3-propanediol, 1,4-butanediol, 1,3-butanediol, 1,2-butanediol, 1,2-pentanediol, 2,4-pentanediol, 2,2-dimethyl-1,3-propanediol, diethyleneglycol, and triethyleneglycol, glycerin, trimethylolpropane, xylitol, arabitol, 1,2- or 1,3cyclopentanediol, 1,2- or 1,3-cyclohexanediol, and 2,3-norbornanediol.

The cumulative amount of polyhydroxyl compounds and carbonyl compounds fed to the reaction vessel are at a molar ratio of polyhydroxyl compounds relative to carbonyl compounds (aldehyde or ketone compounds) of at least 3:1, or at least 4:1, or more than 5:1, or at least 6:1, or at least 7:1, or at least 8:1, or at least 9:1, or at least 10:1, or at least 13:1. There is no particular upper limit. It is economically desirable to limit the amount of polyhydroxyl compounds that need to be separated and recycled balanced against the need to use an excess sufficient to enhance selectivity and yield to the desired cyclic acetal or ketal. Practically, a molar ratio of polyhydroxyl compounds to carbonyl compounds does not need to be more than 30:1, or not more than 20:1, and even not more than 15:1.

The molar ratio of polyhydroxyl compounds to carbonyl compounds is determined by the total amount fed to the reaction vessel. If a recycle stream of polyhydroxyl compounds is fed to the reaction vessel, this quantity should be factored into the molar ratio.

The polyhydroxyl composition and the carbonyl compounds composition may be fed as separate streams or as a combined stream into the reaction vessel. If viscosity variances between the two are sufficiently great, it is desirable to pre-mix at least a portion of the polyhydroxyl composition with at least a portion of the carbonyl compounds to increase the yield and improve the number of contact sites between the aldehyde or ketone functionalities and hydroxyl functionalities. As shown in FIG. 1, a polyhydroxyl composition stream 1 and a carbonyl compound composition stream 2 are pre-mixed in a mixing zone prior to entering reaction vessel through a reactant feed stream 3. It is also possible to feed the recycle stream 10 containing unreacted polyhydroxyl compounds and acid catalyst into the mixing zone to adequately mix and uniformly disperse or dissolve all the carbonyl compounds in the polyhydroxyl composition, especially if the polyhydroxyl composition has a significantly higher viscosity than the carbonyl composition.

Either or both the polyhydroxyl composition and the carbonyl composition may be pre-heated if the viscosity of either or both are too high to provide satisfactory mixing or if either or both are solids at ambient conditions. The polyhydroxyl compounds and the carbonyl compounds should be in the liquid state upon entry into the reaction vessel.

Polyhydroxyl compounds and the carbonyl compounds fed to the reaction vessel are reacted in the presence of a homogeneous acid catalyst. Examples of acid catalyst include Brønsted-Lowry acids. Acids that may be used include hydrochloric acid, sulfuric acid, phosphoric acid, hydrofluoric acid, hydrobromic acid, hydroiodic acid, hyperchloric acid, para-toluene sulfonic acid, and methyl sulfonic acid, triflic acid, trifluoro acetic acid, and tosic acid. These acids can be liquid or aqueous solutions and form a homogeneous phase in the liquid reaction medium.

The acid catalyst may be fed to the reaction vessel separately or premixed into one or both of the polyhydroxyl composition stream(s) 1, the carbonyl composition stream(s) 2, the recycle stream(s) 10, or the reactant stream 3 fed to the reaction vessel. The reaction vessel contains a homogeneous reaction mixture, meaning that the acid catalyst forms a homogeneous solution with other ingredients in the reaction vessel such that the contents of the reaction vessel are a homogeneous liquid phase reaction mixture, as distinguished from a reaction vessel that contains a solid catalyst dispersed in a liquid reaction mixture or a fixed catalyst bed.

The reaction vessel is a vessel that accepts a feed or multiple feeds of the carbonyl compounds and the polyhydroxyl compounds before they are reacted with each other in the presence of the homogeneous catalyst. The reaction vessel may also accept recycle feeds containing carbonyl or polyhydroxyl compounds or homogeneous acid that have already been a part of a reaction mixture in the reaction vessel but are unreacted in the case of the carbonyl or polyhydroxyl compounds. Since the homogeneous catalyst is mobile, it is recognized that reactions may continue to proceed in the distillation vessel and downstream vessels from the distillation column, and these vessels are distinct from the reaction vessel.

The reaction vessel is desirably liquid full and the reaction mixture in the reaction vessel flows in the direction of the feed entry points to the effluent locations. In a horizontal vessel, this can be a horizontal flow from left to right or right to left depending on the feed/effluent configuration. In a vertically oriented vessel, this can be from top to bottom or bottom to top. In one embodiment, the reaction mixture inside the reaction vessel flows in an upward direction of bottom to top. By having the feed entry points at or near the bottom of the reaction vessel and the effluent at the top of the reaction vessel, better mixing is obtained.

The reaction vessel can be contained in any suitable vessel. In one embodiment, the reaction vessel is a pipe or tank having an L/D ratio of more than 1:1, or more than 2:1, or more than 3:1, or more than 4:1, or more than 5:1, or more than 6:1, or more than 7:1, or more than 8:1, or more than 9:1, or more than 10:1.

The reaction vessel may be mechanically agitated. Practically, the reaction vessel is not mechanically agitated. For example, a pipe can be used without mechanical agitation, although if desired the pipe may contain weirs or baffles to provide turbulent flow induced agitation The reaction can proceed well under atmospheric pressure and at elevated pressure. The pressure within the reaction vessel can be at least 0.1 atm, or at least 0.5 atm, or at least 1 atm, or at least 1.05 atm, or at least 1.1 atm, or at least 1.5 atm, or at least 2 atm, or at least 3 atm, or at least 4 atm. For most applications, the pressure does not need to exceed 10 atm, or exceed 5 atm, or exceed 3 atm, or exceed 2 atm.

Inside the reaction vessel, polyhydroxyl compounds react with carbonyl compounds to produce cyclic acetals or cyclic ketals or a mixture thereof, water, and by-products. The cyclic acetal, for purposes of this description, is the desired principal product produced from the reaction of the starting aldehydes and starting polyhydroxyl compounds. The principal product, the cyclic acetal, is the cyclic reaction product of one mole of the starting aldehyde compound with one mole of the starting polyhydroxyl compound releasing one mole of water. Examples of by-products in reaction mixture to make cyclic acetals are aldehyde-aldehyde reaction products, polyhydroxyl-polyhydroxyl reaction products, the secondary reaction products between cyclic acetals with any other reactants or with itself, internal re-arrangement of the cyclic acetal ring and any further reaction products resulting from the ring re-arrangement, or a combination thereof. Since a high molar excess of polyhydroxyl compound is used, unreacted polyhydroxyl compounds will also be present in the reaction mixture. The reaction mixture may also contain unreacted aldehyde compounds.

The same applies to the production of cyclic ketals. The cyclic ketal, for purposes of this description, is the desired principal product produced from the reaction of the starting ketones and starting polyhydroxyl compounds. The principal product, the cyclic ketal, is the cyclic reaction product of one mole of the starting ketone compound with one mole of the starting polyhydroxyl compound releasing one mole of water. Examples of by-products in reaction mixture to make cyclic ketals are ketone-ketone reaction products, polyhydroxyl-polyhydroxyl reaction products, the secondary reaction products between cyclic ketals with any other reactants or with itself, internal re-arrangement of the cyclic ketal ring and any further reaction products resulting from the ring re-arrangement, or a combination thereof. Since a high molar excess of polyhydroxyl compound is used, unreacted polyhydroxyl compounds will also be present in the reaction mixture. The reaction mixture may also contain unreacted ketone compounds.

The yield of a product compound (not by-products or water), whether one desires to determine the yield of cyclic compounds, an acetal compound, or a ketal compound, is determined by dividing the moles of product compounds produced by the moles of reactant fed in the lowest molar quantity, multiplied by 100. For example, the yield of cyclic compounds is determined by dividing the moles of cyclic compounds produced by the moles of corresponding aldehyde and/or ketone compounds fed, multiplied by 100. The yield of cyclic acetal compounds is determined by dividing the moles of cyclic acetal compounds produced by the moles of aldehyde compounds fed, multiplied by 100. The yield of cyclic ketal compounds is determined by dividing the moles of cyclic ketal compounds produced by the moles of ketone compounds fed, multiplied by 100.

Selectivity of cyclic compounds is determined by dividing the moles of cyclic compounds produced by the moles of their respective aldehyde or ketone compounds converted, multiplied by 100. Selectivity to the cyclic acetal is determined by dividing the moles of cyclic acetal compounds produced by the moles of aldehyde compounds converted, multiplied by 100. Selectivity to the cyclic ketal is determined by dividing the moles of cyclic ketal compounds produced by the moles of ketone compounds converted, multiplied by 100.

Conversion to cyclic compounds is determined by dividing the moles of cyclic compounds converted by the moles of the respective aldehyde or ketone compounds fed, multiplied by 100. Conversion to cyclic acetals is determined by dividing the moles of cyclic acetal compounds converted by the moles of aldehyde compounds fed, multiplied by 100. Conversion to cyclic ketals is determined by dividing the moles of cyclic ketal compounds converted by the moles of ketone compounds fed, multiplied by 100.

In the process of the invention, high yields of cyclic compounds are obtainable without the necessity of separating the by-product water from the reaction mixture as it is being formed in the reaction mixture. Even though the reaction is an equilibrium reaction with the presence of water having the capability to hydrolyze the acetal or ketal product and lower yield, the reaction of polyhydroxyl compounds in high molar excess with aldehyde compounds in the presence of the acid keeps the selectivity and yield of cyclic acetal high. This has the advantage that water is not required to be removed by distillation or other means in the reaction vessel as it is being formed in order to obtain high yields. Further, the reaction processing window is widened and not constrained by the boiling point ranges of the reactants and reaction products and by-products.

The cyclic reaction products formed in the reaction mixture contain an acetal moiety or a ketal moiety or both. The cyclic compounds produced in the process of the invention have two oxygen atoms single bonded to the same carbon atom in the ring structure. Suitable cyclic acetal and ketal moieties include 1,3-dioxolane moieties and 1,3-dioxane moieties, although larger ring compounds having oxygen atoms in the 1,3 position are also contemplated.

The cyclic compounds produced in the process of the invention that includes a cyclic acetal moiety or a cyclic ketal moiety may be represented by the general Formula II:

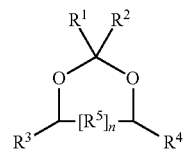

wherein $R^1$, $R^2$, $R^3$, and $R^4$ are independently H; a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cycloalkyl, or a $C_3$-$C_{50}$ carboxylate ester; and wherein $R^1$ and $R^2$ may optionally be bonded to each other through one or more carbon atoms, and wherein $R^1$, $R^2$, $R^3$, and $R^4$ optionally containing 1, 2, or 3 oxygen atoms in the alkyl or alkenyl group, and wherein the alkyl, alkenyl, aryl, and cycloalkyl groups of $R^1$, $R^2$, $R^3$, and $R^4$ are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol;

wherein any one or both of $R^3$ and $R^4$ are optionally independently a hydroxyl, halogen, dialkylamino, amine, aldehyde, ketone, carboxylic acid, ester, ether, alkynyl, dialkylamide, anhydride, carbonate, epoxide, lactone, lactam, phosphine, silyl, thioether, thiol, or phenol;

wherein $R^5$ is branched or unbranched divalent alkyl or divalent alkenyl group each having 1 to 20 carbon atoms and optionally containing 1, 2, or 3 oxygen atoms in the alkyl or alkenyl group and optionally substituted with —OH, halogen, dialkylamino, aldehyde, ketone, carboxylic acid, ester, ether, alkynyl, aryl, dialkylamide, anhydride, carbonate, epoxide, lactone, lactam, phosphine, silyl, thioether, thiol, and phenol; and wherein n is an integer selected from 0 or 1.

$R^1$, $R^2$, $R^3$, and $R^4$ may independently be H, or a branched or un-branched $C_1$-$C_6$ alkyl group. Or, $R^1$, $R^2$, $R^3$, and $R^4$ may independently be H, or a branched or un-branched $C_1$-$C_4$ alkyl group. $R^1$ may be a branched or unbranched $C_1$-$C_6$ alkyl group while $R^2$ is a hydrogen atom to provide a cyclic acetal.

$R^5$ may be a branched or unbranched divalent alkyl group having 1 to 6, or 1 to 4, or 1 to 3, or 1 to 2 carbon atoms.

Particularly useful cyclic acetals for this invention leading to useful materials of commerce include 1,3-dioxolanes having R1 being an alkyl group that can lead to "E-series" type solvents. Likewise, 1,3-dioxolanes having R1 being an alkyl group and R3 being a methyl group can lead to "P-series" type solvents.

Examples of cyclic acetals include 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dixoane, 2-propyl-4-methyl-1,3-dioxane, 5,5-dimethyl-2-propyl-1,3-dioxane, 5,5-dimethyl-2-ethyl-1,3-dioxane, 2-ethyl-1,3-dioxepane, 2-ethyl-1,3,6-trioxocane, 4-methanol-2-propyl-1,3-dioxolane, or 4-methanol-2-propyl-1,3-dioxane, 4-methanol-2-propyl-1,3-dioxolane, and 2-propyl-1,3-dioxane-4-ol.

Examples of cyclic ketals include 2,2-dimethyl-1,3-dioxolane, 2,2-dimethyl-1,3-dioxane, 2,2,4-trimethyl-1,3-dioxolane, 2,2-dimethyl-1,3-dioxepane, 4-methanol-2,2-dimethyl-1,3-dioxane, 2,2-dimethyl-1,3-dioxan-4-ol, 2,2-dimethyl-1,3-6-trioxocane, 2-isopropyl-2-methyl-1,3-dioxolane, 2-isopropyl-2-methyl-1,3-dioxane, 2-isopropyl-2,4-dimethyl-1,3-dioxolane, 2-isopropyl-2-methyl-1,3-dioxepane, 4-methanol-2-isopropyl-2-methyl-1,3-dioxane, 2-isopropyl-2-methyl-1,3-dioxan-4-ol, 2-isopropyl-2-methyl-1,3-6-trioxocane, 2-methyl-2-pentyl-1,3-dioxolane, 2-methyl-2-pentyl-1,3-dioxane, 2,4-dimethyl-2-pentyl-1,3-dioxolane, 2-methyl-2-pentyl-1,3-dioxepane, 2-methyl-2-pentyl-4-methanol-1,3-dioxolane, 2-methyl-2-pentyl-1,3-dioxan-4-ol, 2-methyl-2-pentyl-1,3-6-trioxocane, The reaction mixture is not treated to separate water from the reaction mixture prior to withdrawing the reaction mixture from the reaction vessel. The reaction vessel is liquid full with the liquid in the reaction vessel being well mixed or proceeding in plug flow. The reaction temperature is no particularly limited. The reaction conditions inside the reaction vessel desirably keep the reaction mixture in a liquid state and are not set to exceed the boiling point of the mixture under the reaction conditions. Suitable reaction temperatures are at least −15° C., or at least 0° C., or at least 15° C., or at least 25° C., or at least 30° C., or at least 40° C., and desirably less than 110° C., up to 90° C., or up to 70° C., or up to 50° C.

The reaction mixture is withdrawn from the reaction vessel as a liquid product stream line 4 as illustrated in FIG. 1. The product stream is considered a liquid product stream if water, cyclic compounds, and polyhydroxyl compounds are present in the product stream as a liquid and have not been subjected to temperatures above the boiling point of the mixture in the reaction vessel under reaction vessel conditions.

The liquid product stream removed from the reaction vessel is also a unique composition. There is now provided a liquid composition comprising water, polyhydroxyl compounds, and cyclic compounds, each in the following mole percentages based on the moles of all liquids in the composition:
  a. water: at least 2 mole %, or at least 3 mole %, or at least 6 mole %, or at least 8 mole %, or at least 10 mole %, and up to 35 mole %, or up to 25 mole %, or up to 20 mole %, or up to 15 mole %;
  b. polyhydroxyl compounds: at least 50 mole %, or at least 60 mole %, or at least 65 mole %, or at least 70 mole %, and up to 95 mole %, or up to 90 mole %, or up to 85 mole %;
  c. cyclic compounds: at least 2 mole %, or at least 3 mole %, or at least 5 mole %, or at least 7 mole %, and up to 35 mole %, or up to 25 mole %, or up to 20 mole %, or up to 15 mole %;
  d. acid catalyst: at least 0.01 mole %, or at least 0.1 mole %, or at least 0.2 mole %, or at least 0.25 mole % and up to 5 mole % or up to 4 mole % or up to 3 mole % or up to 2 mole % or up to 1 mole % or up to 0.75 mole %;
wherein the liquid composition optionally contains carbonyl compounds which, if present, do not exceed 20% of the number of moles of cyclic compounds, and wherein the cumulative amount of all liquid ingredient in the liquid composition other than a), b), c), and carbonyl compounds, if present, does not exceed 10 mole %, and the cyclic compounds comprise cyclic acetals, cyclic ketals, or a combination thereof.

The liquid composition optionally contains carbonyl compounds (i.e. aldehyde and/or ketone compounds) which, if present, do not exceed a cumulative amount of 15%, or do not exceed 12%, of the number of moles of cyclic compounds, and wherein the amount of any other liquid ingredient in the liquid composition does not exceed 8 mole %, or does not exceed 6 mole %.

The cyclic compound in the liquid product stream may be a cyclic acetal or a cyclic ketal. The liquid product stream line 4 is fed directly or indirectly to a distillation column to separate the cyclic compounds and water and unreacted carbonyl compounds as one or more overhead product streams and unreacted polyhydroxyl compounds and acid catalyst as one or more bottoms streams. The overhead product stream(s) may be a single overhead product stream as shown in line 5 of FIG. 1 or multiple overhead product streams. The overhead product stream(s) exiting the distillation column is desirably a vapor stream(s). At least a portion of the condensable compounds in these vapor streams are desirably condensed for use as reflux and/or to isolate useful cyclic acetal products and thereafter purify the concentration of the liquid cyclic acetal products through conventional concentration and/or separation techniques.

As shown in FIG. 1, the distillation column has an overhead product stream line 5, which is desirably a vapor when exiting the distillation column and may be condensed if desired. The overhead product stream exiting the column is rich in the concentration by weight of cyclic compounds relative to the concentration by weight of cyclic compounds present in bottoms stream, or in other words, the quantity of cyclic compounds in the overhead product stream is greater than the quantity of cyclic compounds withdrawn from the distillation column as a bottoms stream. It is preferred that the same holds true for water in that water is present in the overhead product stream and the overhead product stream is rich in concentration relative to the concentration in the bottoms stream. By rich is meant a higher concentration (in mole %) in one stream than the concentration of the same ingredient in the comparative stream, and that the concentration is measured against all compounds which condense at 0° C. or higher (condensables). Likewise, the overhead product stream is rich in the molar concentration of unreacted carbonyl compounds relative to the concentration of unreacted carbonyl compounds in the bottoms stream.

While the overhead product stream may contain unreacted polyhydroxyl compounds, the overhead product stream is depleted (concentration by moles is less) in the quantity of this ingredient relative to its quantity (concentration by moles) present in the bottoms stream. Thus, the bottoms stream is enriched in the number of unreacted polyhydroxyl compounds relative to the number present in the overhead product stream. The bottoms stream exits the distillation column as a liquid stream. The bottoms stream may also contain by-products other than water. It is desirable that if by-products are present, that the quantity present in the bottoms stream is greater than the quantity in the overhead product stream.

The number of theoretical stages or plates in the distillation column can be from about 5 to about 100, or about 10-30 plates.

The overhead product stream can be subjected to condensation in a condenser. The condensate is collected in a receiver or reflux drum and optionally separated by any conventional means, such as a decanter. The upper organic rich phase of the condensate in the receiver is withdrawn and recovered as product and can be further processed and purified to isolate a purified cyclic compound stream. The lower phase of the receiver is water rich, withdrawn from the receiver, and sent to a water treatment facility or further processed. Instead of a condenser, the overhead product stream can be fed to a second distillation column to separate water and unreacted carbonyl compounds from the desired cyclic compounds.

Table 1 below illustrates the mole % ranges (concentration ranges) for each ingredient in the overhead product stream removed from the distillation column train and after decanting (including the combination of the aqueous and organic phases), wherein the stated mole % is based on the weight of all ingredients within the overhead stream:

TABLE 1

| Ingredient | Mole % | Mole % | Mole % |
|---|---|---|---|
| Water | 30-50% | 44-50% | 47-49% |
| Unreacted Carbonyl Compounds | 0.1-20% | 2-8% | 4-6% |
| By-Products | 0-10% | 0-5.0% | 1.0-2.0% |
| Cyclic Compounds (acetals, ketals, or a combination) | 30-50% | 40-50% | 43.0-44.0% |
| Polyhydroxyl Compounds | 0-20% | 0-4.0% | 0.5-1.0% |

The values in Table 1 above also apply to the mole % ranges for each ingredient in the overhead product stream, wherein the stated mole percentages are based on the cumulative moles of all fresh feeds entering the process.

The product stream exiting the reaction vessel may optionally be subjected to one or more process steps prior to entering the distillation column.

The bottoms stream 6 can be subjected to further process steps if desired. For example, the unreacted polyhydroxyl compounds and liquid acid catalyst present in the bottoms stream may be separated from the bottoms stream by any conventional separation technique. One such advantageous technique is feeding the bottoms stream to a settling tank and phase separating the unreacted polyhydroxyl compounds from the by-products. The by-products advantageously phase separate as a top layer and can be decanted and removed from the bottom polyhydroxyl/acid catalyst layer as a by-product stream 7 while the bottom polyhydroxyl/acid catalyst layer can be removed at a location below the by-product layer such as depicted in streams 9 and 10. Alternatively, the bottoms stream may be subjected to an extraction separation technique whereby a hydrocarbon extractant acting as a solvent for the more hydrophobic by-products is mixed with the bottoms stream to assist in the separation of the by-products stream. For example, organic solvents may be used in the extraction of byproducts and introduced into an extraction zone through stream 8. Suitable solvents include liquid hydrocarbons with four carbons to more than twenty carbons, saturated and unsaturated, with or without cyclic structures, aliphatic and cyclic ethers, esters, fatty acids, halogenated hydrocarbons, aliphatic nitriles, and aliphatic and aromatic amines. Specific examples of organic solvents include heptane, octane, and nonane.

Often the polyhydroxyl compounds and the acid catalyst are separated from the bottoms stream, at least a portion can be recycled back to the reaction vessel. As shown in FIG. 1, stream 10, a portion or all of the polyhydroxyl compounds and acid catalyst separated from the bottoms stream and exiting the mixer/settler vessel are returned to a mixing zone feeding the reaction vessel. It is desirable to feed the recycle stream 10 to the mixing zone if a mixing zone is present to uniformly disperse the carbonyl compounds in the polyhydroxyl composition. A portion of the polyhydroxyl compounds and acid catalyst separated from the bottoms stream may be purged through stream 9 and further processed to purify and re-use the purge stream.

The process of the invention is capable of producing a cyclic compound yield of at least 80%, or at least 84%, or at least 85%, or at least 86%, or at least 88%, or at least 89%, and up to 100%, or up to 98%, or up to 95%, or up to 90% based on the amount of aldehyde compounds fed to the reaction vessel. The yield can be conveniently determined by measuring the production of cyclic compounds in the overhead product stream removed from the distillation column.

It is desirable to convert at least 80%, or at least 84%, or at least 84%, or at least 86%, or at least 88%, and up to 100%, or up to 98%, or up to 95%, or up to 93% of the aldehyde or ketone compounds.

The selectivity to the cyclic compounds can be at least 90%, or at least 91%, or at least 92%, or at least 93%, or at least 94%, or at least 95%, or at least 96%, or at least 97%, or at least 98%, and up to 100%, or up to 99.5%, or up to 99%.

The process of the invention may be run in a batch mode, a semi-continuous mode, or a continuous mode. In a continuous mode and in a steady state operation, the process of the invention has a capacity of producing at least 70 metric tons/yr of cyclic compounds, or at least 85, or at least 90, or at least 110 metric tons/yr.

The cyclic compounds in the separated cyclic compound stream can be converted through hydrogenolysis to provide the corresponding ether alcohol solvents. For example, the following cyclic acetals 2-propyl-1,3-dioxane, 2-ethyl-1,3-dioxolane, 2-ethyl-1,3-dioxane, 2-methyl-1,3-dioxane, 5,5-dimethyl-2-propyl-1,3-dioxane, 2-ethyl-1,3-dioxepane, 2-ethyl-1,3,6-trioxocane, 4-methanol-2-propyl-1,3-dioxolane, or 2-propyl-1,3-dioxane-4-ol.

are suitable to make their respective solvents ethylene glycol monobutyl ether, 3-butoxy-1-propanol, ethylene glycol monopropyl ether, 3-propoxy-1-propanol, ethylene glycol monoethyl ether, 3-ethoxy-1-propanol, 3-butoxy-2,2-dimethyl-1-propanol, 4-propoxy-1-butanol, and diethylene glycol monobutyl ether, 3-butoxy-1,2-propanediol, and 2-butoxy-1,3-propanediol through hydrogenolysis.

EXAMPLES

The following apparatus was used. A glass, jacketed vessel was used as the reactor. It was maintained as liquid full by using an up-flow orientation. A distillation column was also used. The distillation column had two sections each being 1" vacuum-jacketed glass columns filled with 0.24" Pro-Pak distillation random packing. The upper section had 15" of packing, while the lower section had 30" of packing. The bottom reboiler was a 1-liter glass, hot-oil jacketed vessel attached to the bottom of the lower column section. The top of the upper section was connected to a glass, jacketed, reflux splitter with a magnetic swing-arm controller and a glass, jacketed condenser. The attached vent hose was connected to an ice trap, pressure controller, and vacuum pump. Teflon tubing was used to connect equipment. The base of the column reboiler was connected by tubing to a positive displacement pump.

The tubing from the discharge of this pump was connected to a separation zone, which was comprised of a mixer and settler. A glass feed vessel contained a solvent. This solvent feed vessel was connected to a positive displacement pump. The tubing from this pump and the tubing from column bottom pump are connected together. This combined stream was connected to a mixer. The mixer was a glass, 30-ml vessel maintained liquid-full which contained a magnetically-driven stirrer. The product stream from the mixer was connected to a 120-ml glass, jacketed vessel, which was a settler. This vessel had two exit ports, one on the top and one on the bottom. During operations, it was maintained liquid full. Its jacket temperature set point was maintained at 90° C. The top port was connected to another positive displacement pump capable of removing material enriched in solvent and byproduct. The bottom port was connected by tubing to feed-material pumps described below.

Glass feed vessels were used which contained aldehyde feed material and polyol feed material, separately. Each was connected by tubing to a positive displacement pump. Tubing from these two feed-material pumps and tubing from the mixer/settler were connected together. The combined stream was connected to a glass, 30-ml liquid-full vessel which contained a magnetically-driven stirrer. This mixed stream was connected to be bottom of the reactor vessel, completing the liquid circuit. A process control system was utilized to monitor temperatures and pump flow rates, and to control the distillation column reflux splitter, using a column temperature setpoint. In each example, n-butyraldehyde was used as the carbonyl compound at a feed rate of 1 ml/min, ethylene glycol was used as the polyhydroxyl compound at a feed rate of 1 ml/min, and the feed rate of unconverted recycled material was 8 ml/min. Liquid acid catalyst was initially charged yet was not added during the experiments.

Example 1

Phosphoric Acid, 40° C., Octane Solvent 1.8 g of phosphoric acid was added to 400 g of ethylene glycol, and the solution was charged into the base of the distillation column. The reactor jacket oil-bath temperature was set to 40° C. Octane, used as the mixer/settler solvent, was added continuously, intermittently into the mixer, and an octane stream enriched in reaction byproducts was removed from the settler. The process ran continuously for 25 hours. The overall conversion, selectivity, and yield to the production of 2-propyl-1,3-dioxolane were high: 91.7%, 98.5%, and 90.3%, respectively.

Example 2

Phosphoric Acid, 22° C., Octane Solvent

The process described in Example 1, continued to operate, but the reactor jacket oil-bath temperature was set to room temperature, 22° C. The only catalyst in the process was what remained from Example 1. The process ran continuously for 24 hours. The overall conversion, selectivity, and yield to the production of 2-propyl-1,3-dioxolane were high: 86.8%, 99.3%, and 86.2%, respectively.

Example 3

Phosphoric Acid, 40° C., Heptane Solvent

The process described in Example 2, continued to operate, but the reactor jacket oil-bath temperature was set to 40° C. The only catalyst in the process was what remained from Example 2. In place of octane, heptane was used as the mixer/settler solvent. The process ran continuously for 53 hours. Since the catalyst was re-used from the previous two examples, the accumulated catalyst operating time was 102 hours. The conversion data showed no decrease, indicating no loss in catalyst activity. The overall conversion, selectivity, and yield to the production of 2-propyl-1,3-dioxolane were high: 91.0%, 99.6%, and 90.6%, respectively.

We claim:

1. A process for making a cyclic compound composition comprising:
    a. feeding a carbonyl composition comprising an aldehyde compound, a ketone compound, or a combination thereof, and a polyhydroxyl composition comprising a polyhydroxyl compound, to a reaction vessel at a molar ratio of all polyhydroxyl compounds to all carbonyl compounds fed to the reaction vessel of at least 3:1; and
    b. in a reaction vessel, reacting the carbonyl composition with the polyhydroxyl compound in the presence of a homogeneous acid catalyst to generate a liquid phase homogeneous reaction mixture in the reaction vessel comprising cyclic compounds, water, acid catalyst, and unreacted polyhydroxyl compound, and wherein at least 80% of the aldehyde, ketone, or combination of aldehyde and ketone compounds fed to the reaction vessel are converted in the reaction vessel, and wherein the reaction conditions within the reaction vessel do not boil the reaction mixture within the reaction vessel; and
    c. without separating water from the reaction mixture as it is being formed in the reaction mixture, continuously withdrawing the liquid phase homogeneous reaction mixture from the reaction vessel as a liquid product stream; and
    d. feeding the liquid reaction product stream directly or indirectly to a distillation column to separate cyclic compounds from unreacted polyhydroxyl compounds and withdrawing from the distillation column an overhead product stream and a bottoms stream, wherein the overhead product stream comprises cyclic compounds, unreacted carbonyl compounds and water and is rich in the concentration of cyclic compounds by moles relative to the bottoms stream, and the bottoms stream comprises unreacted polyhydroxyl compounds and acid catalyst and is rich in the concentration of unreacted polyhydroxyl compounds by moles relative to the overhead product stream;
    wherein the selectivity to cyclic compounds in the overhead product stream is at least 80%.

2. The process of claim 1, wherein at least a portion of unreacted polyhydroxyl compounds are recycled back to the reaction vessel.

3. The process of claim 1, wherein the bottoms stream further comprises reaction by-products, and wherein the reaction by-products are separated from unreacted polyhydroxyl compounds to produce a polyhydroxyl rich stream and a by-product rich stream.

4. The process of claim 1, wherein the carbonyl composition comprises carbonyl compounds represented by Formula I:

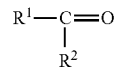

in which $R^1$ and $R^2$ are independently hydrogen or a $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, and wherein $R^1$ and $R^2$ are optionally connected through one or more carbon atoms, and wherein the alkyl, alkenyl, aryl, and cycloalkyl groups of $R^1$ and $R^2$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof.

5. The process of claim 4, wherein the carbonyl compounds comprise acetaldehyde, propionaldehyde, butyraldehyde, isobutyraldehyde, pentaldehyde, 2-methylbutyraldehyde, 3-methylbutyraldehyde, hexaldehyde, heptaldehyde, benzaldehyde, 2-ethylhexaldehyde, octanal, nonanal, 1,3-cyclohexanedicarboxaldehyde, 1,4-cyclohexanedicarboxaldehyde, or combinations thereof.

6. The process of claim 4, wherein the polyhydroxyl compounds comprise ethylene glycol, 1,2-propanediol, 1,3-propanediol, 1,4-butanediol, 1,3-butanediol, 1,2- butanediol, 1,2-pentanediol, 2,4-pentandiol, 2,2-dimethyl-1,3-propanediol, diethyleneglycol, and triethyleneglycol, glycerin, trimethylolpropane, xylitol, arabitol, 1,2- or 1,3cyclopentanediol, 1,2- or 1,3-cyclohexanediol, 2,3-norbornanediol, or combinations thereof.

7. The process of claim 4, wherein the carbonyl compounds comprise propionaldehyde, butyraldehyde, isobutyraldehyde, 2-ethylhexaldehyde, 1,3-cyclohexanedicarboxaldehyde, 1,4-cyclohexanedicarboxaldehyde, or combinations thereof, and the polyhydroxyl compound comprises ethylene glycol, 1,2-propanediol, 1,3-propanediol, 1,4-butanediol, 1,3-butanediol, 1,2- butanediol, diethyleneglycol, or combinations thereof.

8. The process of claim 4, wherein the carbonyl compounds comprise acetone, methyl ethyl ketone (2-butanone), methyl propyl ketone (2-pentanone), methyl isopropyl ketone (3-methyl-2-butanone), methyl isobutyl ketone (4-methyl-2-pentanone), 2-hexanone, 2-heptanone (methyl amyl ketone), 2-octanone, and acetophenone.

9. The process of claim 1, wherein said molar ratio is at least 5:1.

10. The process of claim 1, wherein the carbonyl compounds comprise 1,4-cyclohexanedicarboxaldehyde.

11. The process of claim 1, wherein the reaction vessel contains a homogeneous acid catalyst that is a Bronsted-Lowry acid catalyst.

12. The process of claim 11, wherein the reaction vessel is liquid full.

13. The process of claim 12, wherein the reaction mixture flows in an upward direction in a vertically oriented reaction vessel.

14. The process of claim 13, wherein the reaction vessel is a pipe.

15. The process of claim 1, wherein the cyclic compounds contain a moiety represented by the Formula II:

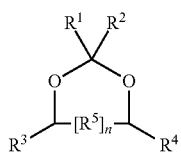

wherein $R^1$, $R^2$, $R^3$, and $R^4$ are independently H; a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cycloalkyl, or a $C_3$-$C_{50}$ carboxylate ester; and wherein the alkyl, alkenyl, aryl, and cycloalkyl groups of $R^1$, $R^2$, $R^3$, and $R^4$, wherein $R^1$ and $R^2$ may optionally be bonded to each other through one or more carbon atoms, and wherein $R^1$, $R^2$, $R^3$, and $R^4$ optionally containing 1, 2, or 3 oxygen atoms in the alkyl or alkenyl group, and optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol;

wherein any one or both of $R^3$ and $R^4$ are optionally independently a hydroxyl, halogen, dialkylamino, amine, aldehyde, ketone, carboxylic acid, ester, ether, alkynyl, dialkylamide, anhydride, carbonate, epoxide, lactone, lactam, phosphine, silyl, thioether, thiol, or phenol;

wherein $R^5$ is branched or unbranched divalent alkyl or divalent alkenyl group each having 1 to 20 carbon atoms and optionally containing 1, 2, or 3 oxygen atoms in the alkyl or alkenyl group and optionally substituted with —OH, halogen, dialkylamino, aldehyde, ketone, carboxylic acid, ester, ether, alkynyl, aryl, dialkylamide, anhydride, carbonate, epoxide, lactone, lactam, phosphine, silyl, thioether, thiol, and phenol; and wherein n is an integer selected from 0 or 1.

16. The process of claim 1, wherein the cyclic compounds comprise 2-propyl -1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dixoane, 2-propyl-4-methyl- 1,3-dioxane, 5,5-dimethyl -2-propyl-1,3-dioxane, 5,5-dimethyl-2-ethyl-1,3-dioxane, 2-ethyl-1,3-dioxepane, 2-ethyl-1,3,6-trioxocane, 4-methanol-2-propyl-1,3-dioxolane, or 4-methanol-2-propyl-1,3-dioxane or combinations thereof.

17. The process of claim 1, wherein the liquid acid comprises hydrochloric acid, sulfuric acid, phosphoric acid, hydrofluoric acid, hydrobromic acid, hydroiodic acid, hydroperchloric acid, para-toluene sulfonic acid, methyl sulfonic acid, triflic acid, trifluro acetic acid, tosic acid, or combinations thereof.

18. The process of claim 1, wherein the temperature in the reaction vessel ranges from 15° C. to 70° C.

19. The process of any one of claims 1-17 and 18, wherein the process is continuous and the yield of cyclic compounds is at least 80%.

20. The process of claim 1, wherein the yield of cyclic compounds in the overhead product stream is at least 85%.

21. The process of any one of claims 1-10, 15-17, 18 and 20, wherein the reaction vessel is liquid full.

22. The process of any one of claims 1-10, 15-17, 18 and 20, wherein all of the reaction mixture flows in an upward direction in a vertically oriented reaction vessel.

* * * * *